United States Patent [19]

Bristow et al.

[11] Patent Number: 4,651,744
[45] Date of Patent: Mar. 24, 1987

[54] SOFT TISSUE EXAMINATION METHOD AND APPARATUS

[75] Inventors: Donald L. Bristow, Ellington; Milton Stoller, West Hartford, both of Conn.

[73] Assignee: Spectrascan, Inc., South Windsor, Conn.

[21] Appl. No.: 719,899

[22] Filed: Apr. 4, 1985

[51] Int. Cl.⁴ .............................................. A61B 10/00
[52] U.S. Cl. ...................................... 128/660; 128/664; 128/665
[58] Field of Search ............................... 128/660-661, 128/664-665; 73/625; 358/111

[56] References Cited

U.S. PATENT DOCUMENTS 4,543,959 10/1985 Sepponen ........................... 128/660 X

OTHER PUBLICATIONS

Ophir, J. et al, "DSCs in Diagnostic UTS Imaging", Proc. IEEE, vol. 67, No. 4, Apr. 1979 (pp. 654-664).
Hoshino, H. et al, "Microprogrammable UTS Image Processor and Its Applications to Image Manipulation", Proc. Soc. Photo-Opt. Instrument Engrg (USA), vol. 314, Digital Radiography 1981, pp. 354-361.

Primary Examiner—Kyle L. Howell
Assistant Examiner—Francis J. Jaworski
Attorney, Agent, or Firm—Chilton, Alix & Van Kirk

[57] ABSTRACT

An ultrasound adapter is provided for a medical diagnostic device which implements a transillumination modality. The ultrasound adapter enables the sharing of data processing circuitry between the transillumination and ultrasound modalities. When in use, the ultrasound adapter provides image data at a rate and in a format which corresponds to that produced by the image sensor of the transillumination instrumentality.

7 Claims, 2 Drawing Figures

SOFT TISSUE EXAMINATION METHOD AND APPARATUS

BACKGROUND OF THE INVENTION (1) Field of the Invention

The present invention relates to non-destructive testing and particularly to a medical diagnostic technique wherein soft body tissue may be serially examined at the same examination site by two different modalities neither of which requires invasion of body or the use of ionizing radiation. More specifically, this invention is directed to apparatus which employs low intensity light and ultrasonic energy to obtain information on the nature of an object being examined and particularly to medical diagnostic apparatus which produces a display commensurate with the amount of absorption at each point in soft tissue under examination of light at different wavelengths and a display commensurate with the ultrasonic energy reflected from the boundaries of regions within the tissue which are characterized by different impedances to passage of ultrasonic energy. Accordingly, the general objects of the present invention are to provide novel and improved methods and apparatus of such character.

(2) Description of the Prior Art

While not limited thereto in its utility, the present invention has particular significance as a breast examination device and method. A recent technological advance in the examination of breast and other soft body tissue consists of transilluminating the tissue with light at a plurality of selected different wavelengths and using digital computation techniques to determine the transmissivity at each selected wavelength of the transilluminating light at each point of the tissue within the viewing field. The computed transmissivity, i.e., the degree of absorption of the light at each transilluminating wavelength, is subsequently employed to create a multi-color image wherein the different colors of the display will be indicative of the nature of the tissue. Examples of such transillumination techniques and apparatus may be seen from U.S. Pat. Nos. 4,467,812 and 4,495,949 and from co-pending application Ser. Nos. 620,271 and 621,194. These patents and pending applications are all assigned to the assignee of the present invention and the disclosures of the pending applications are incorporated herein by reference.

Ultrasonic diagnostic techniques for imaging soft tissue are well-known in the art. As is the case with transillumination, ultrasonic imaging has the advantages that it is a non-invasive technique and does not require ionizing radiation. In ultrasonic imaging a fraction of the energy produced by a transducer is reflected when the transmitted energy encounters a change in the characteristic impedance to the passage of ultrasonic energy. The characteristic impedance of the tissue may be defined as a product of the density of the tissue multiplied by the velocity of sound. The energy reflected from the boundaries between regions having different characteristic impedance may be computer processed and a display produced which provides valuable information to the diagnostician. Examples of prior ultrasonic diagnostic systems may be seen from U.S. Pat. Nos. 4,137,777, 4,207,772 and 4,242,911.

Each of the available imaging modalities which is non-invasive and does not employ ionizing radiation, i.e., transillumination and ultrasonic imaging, has advantages and limitations. Thus, transillumination has the ability of providing a "global" view, wherein abnormal areas may be seen, in a relatively short time. A trained technician employing the transillumination techniques and apparatus of the above-referenced patents and applications can detect very small, i.e., non-palpable, lesions. Transillumination cannot, however, provide information as to the depth within the tissue, i.e., the precise location, of an abnormality since the information containing display is essentially produced from shadows which appear at the surface of the tissue being examined. Also, it is not always possible to differentiate between cystic and solid lesions when applying the transillumination modality. Ultrasonic imaging techniques, on the other hand, are not well-suited for survey or global-type studies because the modality, by its very nature, gives a plane of information. Accordingly, in order to obtain the same information using ultrasound as can be obtained through use of transillumination; information would have to be collected in more than one hundred planes. This, of course, would be much too time consuming to be practical. Ultrasound does, however, have the unique ability to precisely locate abnormalities, and particularly lesions, once they have been detected by some other modality. Ultrasound also has the ability to differentiate between cystic and solid lesions with a very high degree of accuracy. Further, when two lesions are located in very close proximity to each other, a well-focused beam of ultrasonic energy will provide information which enables both lesions to be detected and classified.

It would, of course, be possible to serially examine a patient first employing the transillumination modality and then, if the results of the initial examination indicated it to be necessary or desirable, to re-examine using the ultrasound modality. In the past, the available apparatus which employed the transillumination and ultrasound modalities were "stand-alone" type equipment which, while available in a well-equipped radiology department, would be at different examination sites and would be unable to communicate with one another. Thus, the inconvenience of moving the patient from one examination site to another had to be accepted. Perhaps of more significance, it was extremely difficult to provide the radiologist simultaneously with the results of the transillumination and ultrasound techniques so that a side-by-side comparison could be made. The latter problem was aggravated by the different degrees of resolution of the apparatus for implementing the two modalities and by the different rates at which data is collected during the use of the two modalities.

SUMMARY OF THE INVENTION

The present invention overcomes the above-briefly discussed and other deficiencies and disadvantages of the prior art by permitting an object of interest to be serially tested, at the same site, employing transilluminated light and ultrasonic energy. Apparatus in accordance with the invention is characterized by economic and volumetric efficiency and particularly by the sharing of hardware for processing of signals provided by an ultrasound transducer and a multi-spectral light generator and associated sensor. Thus, in accordance with the invention, information obtained through an examination with ultrasonic energy will be processed using a portion of the computation system which is employed to process data collected by means of transillumination of the same tissue.

BRIEF DESCRIPTION OF THE DRAWING

The present invention may be better understood and its numerous objects and advantages will become apparent to those skilled in the art by reference to the accompanying drawing wherein like reference numerals refer to like elements in the FIGURES and in which.

DESCRIPTION OF THE DISCLOSED EMBODIMENT

Figure 1:
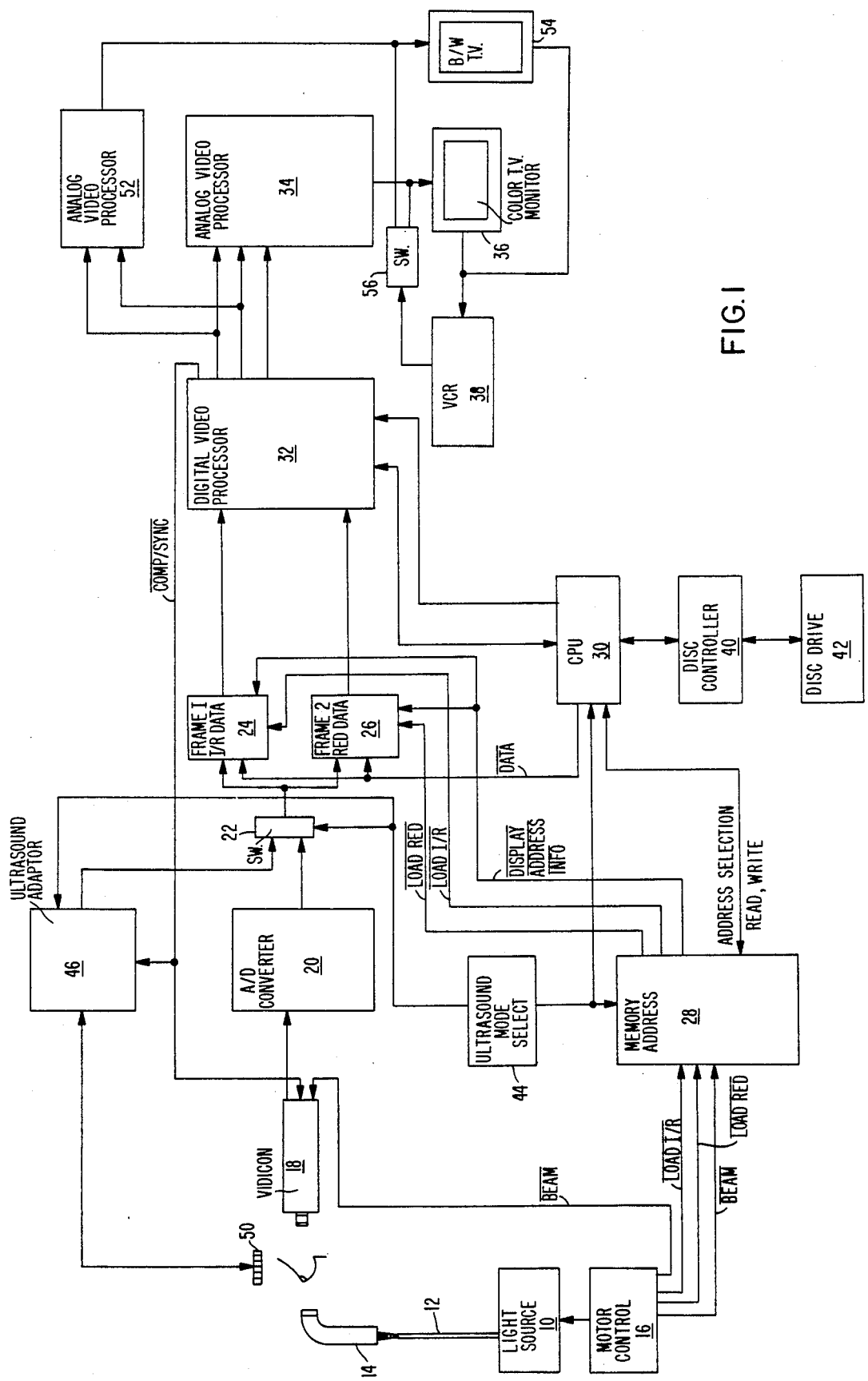
FIG. 1 is a functional block diagram which depicts a preferred embodiment of the present invention.

With reference to FIG. 1, and first describing the present invention in the implementation of the transillumination modality, light in the red and near infrared spectra provided by a light source 10 is employed for transilluminating human body tissue. The light source 10 may, for example, comprise a system such as shown in FIGS. 4 and 5 of the above-referenced co-pending applications. Light at the selected wavelengths will be alternately delivered, via a bundle of optical fibers 12, from source 10 to a "wand" 14 having a light emitting end which is placed against or in close proximity to the tissue to be examined. The control for the motor which imparts rotation to a filter and shutter included within source 10 is indicated at 16. Operation of the data processing system must be synchronized with the transillumination of the tissue being examined with the light at the selected wavelengths. Accordingly, the motor control 16 will produce timing control signals which will have the effect of determining when data is collected and when and where the collected data is stored. These timing control signals are indicated as "BEAM", "LOAD RED" and "LOAD I/R".

During operation of the invention in the transillumination mode, with the tissue under examination being alternately illuminated with light having a frequency in the red and infrared range, a color video camera 18 will be focused on the breast or other object being examined. Camera 18 will typically include a silicon face plate tube that is responsive in the region of from 650 nanometers to 900 nanometers. Camera 18 will receive short bursts of light, when the tissue under examination is being illuminated, which have the effect of discharging, in varying degrees, the surface of the silicon face plate in the camera tube. The scanning cycle is divided into six segments. During a first segment the tissue being examined is illuminated with light of a first wavelength and the surface of the face plate of the camera tube discharged. During a second segment the partially discharged tube surface is scanned with an electron beam and, in the conventional manner, an analog video signal appears at the camera output terminals. During a third segment the camera tube is recharged. Thereafter, during the fourth segment the camera tube is discharged as a consequence of exposure to light at the second wavelength, during the fifth segment the camera tube is again read-out and during the sixth segment the camera tube is recharged. The synchronizing of the camera 18 with the light source results from the delivery of the "BEAM" signal from motor control 16 to camera 18. During read-out the camera 18 is "slaved" to a digital video processor which includes a master system oscillator which provides the synchronizing signals for controlling the scanning of the camera tube surface by the electron beam.

The analog video signals provided by of camera 18 are delivered to an analog-to-digital converter 20. The digital output signals from converter 20 are passed via a switching circuit 22 to the appropriate one of a pair of frame memories 24 and 26. Thus, in the example shown, the digitized data commensurate with the transilluminated light in the red frequency range will be loaded into memory 26 while the data commensurate with the transilluminated light in the infrared frequency range will be loaded into memory 24. The memories 24 and 26 may, for example, comprise dynamic memory elements having 8 bits of memory for each picture location, i.e., each pixel.

The routing of data to memories 24 and 26 is controlled by a memory address generator 28. The memory address generator 28 comprises counters and switching circuitry. Thus, in response to the timing control signals provided by motor control 16, the memory address generator 28 will provide appropriately timed enabling signals for memories 24 and 26 as well as address information which determines where in the enabled memory the digitized data read out of camera 18 will be stored.

The information temporarily stored in memories 24 and 26 is simultaneously "read" by a digital video processor 32. Digital processor 32 will perform the function of elements 44, 50 and 52 of the above-referenced patents. Thus, digital video processor 32 will include a random access memory in which numbers corresponding to the intensity of two colors, typically red and green, will be stored. The stored numbers will be commensurate with all of the possible ratios of the numbers which may be stored at the same memory location in each of memories 24 and 26. Thus, the numbers stored at the corresponding memory locations in memories 24 and 26 are employed to address the RAM in processor 32 whereupon the processor will produce a pair of color related, digitally coded output signals for each pixel. The digital video processor 32 also provides a digitized average luminance signal.

The three digital signals produced in processor 32 are delivered to an analog video processor 34. Processor 34 will convert the color related output signals from processor 32 to analog chrominance output signals which, in the example being described, will correspond to a red intensity and a green intensity. These intensity signals, and the average luminance signal, which is also first processed in a digital-to-analog converter, are further processed to provide a single modulated carrier signal which may be employed as the input to a color TV monitor 36. Thus, analog video processor 34 performs the function of elements 54, 56, 58, 60, 62 and 64 of the above-referenced patents.

In the conventional manner, the video signal displayed on monitor 36 may also be delivered to a video cassette recorder 38 for storage. The digital data appearing at the output of processor 32 may also be stored for future processing through the apparatus. For this purpose, the system includes a disc controller 40 and associated disc drive 42. Thus, rather than storage on tape, information with respect to a patient may be stored on a "floppy" disc which may conveniently be placed in the patient's file.

For a further description of the operation of the present invention in the transillumination mode, reference may be had to U.S. Pat. Nos. 4,467,812 and 4,495,949 and the two co-pending applications which have been incorporated herein by reference.

A novel feature of the present invention comprises the addition to the transillumination apparatus, as described above, of the capability for ultrasonic imaging. When in the ultrasound mode, which is activated by the operation of an ultrasound mode select switch 44, an ultrasound transducer 50 will be energized. The transducer 50 will be a phased-array type device which is electronically controlled so as to produce a beam of ultrasound energy which will be focused at plural depths within the object being examined. The transducer will be mounted within a head and will be scanned linearly by a drive motor. For a general discussion of the construction and excitation of phased-array ultrasound generators, reference may be had to U.S. Pat. No. 4,207,772. The means for controlling transducer 50 and for processing the analog signals commensurate with echos received at the transducer are included in an ultrasound adaptor 46 which will be discussed in detail below in the description of FIG. 2. The adaptor 46 receives an "on" command from mode select switch 44. This same command signal, when switch 44 is in the ultrasound mode, excercises control over switching circuit 22 whereby the output of analog-to-digital converter 20 is isolated from memories 24 and 26 and the output of adaptor 46 will be connected to one of memories 24, 26. A command signal from ultrasound mode select switch 44 is also delivered to the memory address generator 28 and a computer (CPU) 30 whereupon memory addresses and an enable signal will be generated, under the control of CPU 30, which will permit loading of ultrasound image data from adaptor 46 into one of frame memories 24, 26. The CPU will also, when the ultrasound mode is selected, load a special luminance table into the memory in digital video processor 32. Digital data outputted from processor 32 is delivered to a black and white analog video processor 52. Processor 52 includes digital-to-analog convertors and conventional modulation circuitry whereby the information read from memories 24 and 26 in the ultrasound mode will be converted into a video signal which is delivered to a conventional black and white TV monitor 54. Processor 52 differs from processor 34 by lacking color capability and by having greater bandwidth.

The above-mentioned CPU 30 includes memories and input/output devices. CPU 30 controls many functions, including self-testing, which will not be described herein. When in the ultrasound mode, CPU 30 changes the system architecture such that all image data is loaded into one of memories 24, 26, as described above, while the other memory becomes a graphics plane for annotation and for calipers. The information which forms the graphics plane or overlay is partly pre-programmed into CPU 30 and may partly be entered by means of a keyboard or similar data entry device, not shown. In the caliper mode, which is known in the art, additional data is loaded into the memory which contains the information which defines the graphics plane. This additional data comprises a pair of movable cursors with the position of the cursors being fed back to CPU 30 whereby the distance therebetween will be computed and subsequently displayed. Thus, in the ultrasound mode, CPU 30 interacts with memories 24 and 26 and with memory address generator 28. In the course of such interaction, CPU 30 provides memory address generator 28 with address selection, read, write and memory request commands.

It is to be noted that, when in the ultrasound mode, the digital data being delivered to video signal processor 52 may be stored on the same disc which has received the data collected during the transillumination examination. Additionally, the signals delivered to TV monitor 54 may be recorded by VCR 38 on the same tape with the transillumination images. In either event, the radiologist is provided with the ability to analyze the results of the examinations employing both transilluminated light and ultrasound at the same time and in the same location.

Figure 2:
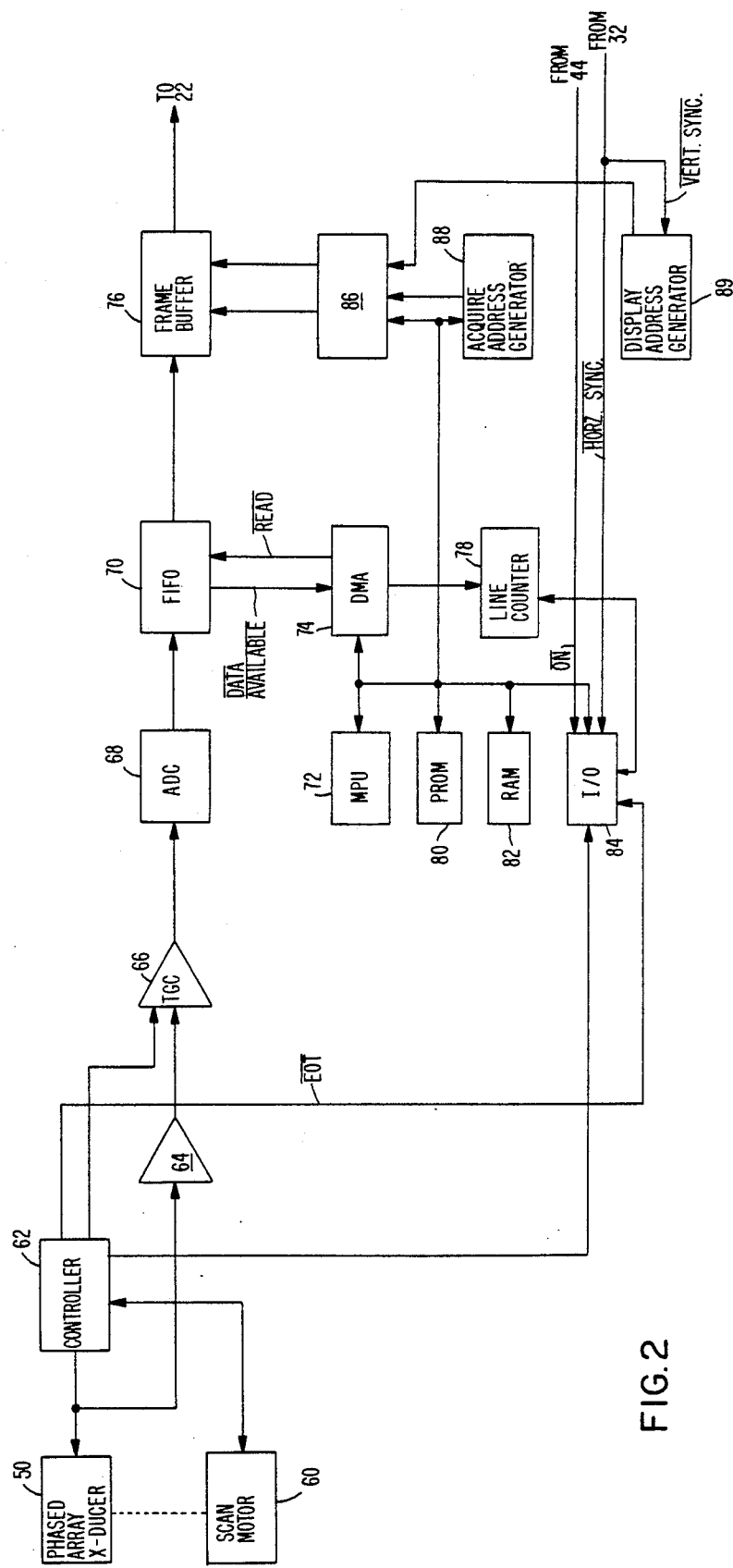
FIG. 2 is a functional block diagram of the ultrasound adaptor of the embodiment of FIG. 1.

Referring now to FIG. 2, the ultrasound adaptor 46 is shown in functional block diagram form. As noted above, the transducer 50 is a phased-array type device which is characterized by multiple zone focus. In one reduction to practice of the invention the piezoelectric crystal of the ultrasound generator was electronically controlled so as to be serially focused at four different focal lengths or zones for each position of the transducer, the transducer being linearly scanned back and forth by a stepping motor 60. Unlike a television scan, which has a fly-back portion during which data is not collected, the ultrasound transducer collects data in both scan directions. The construction of transducer 50 and the means 62 by which control is exercised thereover are known in the art and will not be further described herein.

Analog signals commensurate with the echos received at transducer 50 are amplified in a pre-amplifier 64 and delivered as an input to a further amplifier 66. Amplifier 66 provides time/gain compensation and, for this purpose, receives a gain control signal from controller 62. The employment of time/gain compensation, i.e., the variation of amplification inversely to the length of travel of the ultrasound energy, is a common technique in ultrasonic imaging and will not be further described herein. The gain compensated echo-related signals from amplifier 66 are converted to digital signals in an analog-to-digital converter 68 and the digital data is serially inputted to a first-in first-out memory (FIFO) 70 which, in one reduction to practice, had a capacity of 512 bytes, i.e., the capacity of the FIFO 70 is somewhat greater than one line of data. As used herein the term "line" refers to all samples of ultrasound data, i.e., all pixels, collected at each position of the transducer 50 along a scan line. In the example being described, where the transducer is focussed at four (4) different points for each position of motor 60, each line comprised 312 range samples with each sample having eight (8) bits of resolution. The digitized data from the ultrasound scan is clocked into FIFO 70 in synchronism with its collection.

The ultrasound adaptor 46 is provided with its own dedicated microprocessor (MPU) 72 which excercises control over the manipulation of the digitized data resulting from an ultrasound scan. Upon receipt of an "ON" command signal from ultrasound mode selector 44, the MPU 72 will generate an initialize command which is delivered to a direct memory access logic controller (DMA) 74. DMA 74 is a high speed device for moving data from one location to another and comprises a set of counters and associated timing logic. DMA 74 is also coupled to FIFO 70 and to a line counter 78. Line counter 78 counts the number of data samples transferred from FIFO 70 into a frame buffer 76. Counter 78 will be initialized by MPU 72 upon energization of the ultrasound mode and, by way of example, incremented as FIFO 70 is unloaded and reset after a line of data has been transferred out of FIFO 70. Counter 78 thus tells MPU 72 when a line of data has been transferred from FIFO 70. In the known manner, a PROM 80, RAM 82 and input/output control 84 are associated with MPU 72.

A primary function of ultrasound adaptor 46 is to present digital data to one of the frame memories 24, 26 in such a manner that the data appears to have been generated by a TV camera, i.e., by camera 18. Accordingly, it is necessary to convert the data which is serially loaded into FIFO 70 to an output stream of data synchronized with the scanning of the tube in camera 18. This is accomplished by transferring data from the FIFO 70 into appropriate memory locations in frame buffer 76 and thereafter reading the data from the frame buffer 76 into one of the frame memories 24, 26 at the TV camera scan rate.

The frame buffer 76 includes input latches, a memory and output latches. In one reduction to practice, the memory of frame buffer 76 had a capacity of 64K by 8 bits. Frame buffer 76 is controlled by DMA 74 so as to have alternate acquire and display cycles. The mode of operation, i.e., acquire or display, corresponds to the state of a three-way switch 86. Switch 86 is shown as being connected to MPU 72, "ACQUIRE" address generator 88 and a "DISPLAY" address generator 89. In actual practice, address generator 88 is part of DMA 74. The frame buffer is switched to the acquire mode by the appearance of a "data available" signal at the output of FIFO 70, the "data available" signal indicating that a data sample is available to be transferred to frame buffer 76. Completion of the transfer will cause line counter 78 to be incremented and, as noted above, MPU 72 will reset counter 78 when a line of data has been transferred from FIFO 70.

During the display mode, data from FIFO 70 is shifted into the input data latches of frame buffer 76. Subsequently, during the acquire cycle of DMA 74, the data in the frame buffer input latches is written to the appropriate location in the frame buffer 76 and line counter 78 incremented. The addresses at which the data samples are stored in frame buffer 76 are generated by address counters in DMA 74 and applied to the frame buffer 76 address bus. As noted above, in the interest of facilitating understanding of the invention, the system is depicted as including a separate "ACQUIRE" address generator 88 wherein address generator 88 is part of DMA 74. The DMA 74 also generates the "write" pulse for frame buffer 76.

The data acquired during ultrasound imaging has more resolution in range, i.e., depth, than in ozimuth. A television display has greater resolution in the horizontal direction than in the vertical direction. It would, of course, be desirable to match the maximum resolution of the display with that of the imaging modality. This is accomplished in the present invention by exercising control over the storage locations in frame buffer 76 where the ultrasound data is written. The MPU 72 keeps track of where the ultrasound data is acquired, i.e., where each "line" begins and ends. MPU 72 presets the address counters in acquire address generator 88 before enabling the DMA logic. Address generator 88 addresses frame buffer 76 such that the locations of storage of ultrasound image data, i.e., the data commensurate with the echos returned to the transducer, will be commensurate with the position along a scan line where such data has been acquired and will be on the horizontal scan axis of the monitor when the contents of the frame buffer are displayed. Accordingly, the collected data will be stored at the proper memory locations in frame buffer regardless of the direction of scan of the ultrasound transducer 50, i.e., the data collected during both directions of scan of the transducer is utilized.

During the display mode, i.e., during the reading of data from the frame buffer 76 into one of the frame memories 24, 26 and the simultaneous shifting of data from FIFO 70 into the input latches of frame buffer 76, the frame buffer memory will be addressed by address information provided by display address generator 89 via switch 86. This addressing, i.e., the read-out of the frame buffer 76, will be at the same rate as the scanning of the TV camera tube during the transillumination mode. The synchronizing signals for the frame buffer read-out operation are provided by the master oscillator in digital video processor 32, the vertical synchronization signal provided by the digital video processor being employed for this purpose. The horizontal synchronization signal from the master oscillator in digital video processor 32 is supplied, via the input/output device 84, to the microprocessor 72 and is used to generate the MPU clock signals.

Thus, to summarize the above, the ultrasound image data, after digitization, is serially clocked into FIFO 70 at the data collection rate. In one reduction to practice of the invention, 312 samples of data, each having 8 bits of resolution, were collected at each position of transducer 50. The data clocked into the FIFO was transferred into the frame buffer 76. The frame buffer has the capacity of holding one full frame of data. Under the control of the display address generator 89, the data in frame buffer 76 is read into one of frame memories 24, 26 at the scan rate of the TV camera of the transillumination apparatus and thus the incoming data from the ultrasound adaptor 46 appears to the transillumination apparatus as having been produced by a TV camera. The ultrasound image data, and the overlay, are subsequently serially processed in video processors 32 and 52 and a black and white TV display produced on monitor 54.

As described above, the present invention matches the resolution of the imaging modality to that of the display device. Accordingly, the range information is displayed along the horizontal sweep axis of the monitor. While maximum resolution is achieved, this would provide a display wherein depth within the object being examined would lie on horizontal axes. In order to facilitate interpretation of the display, in accordance with the present invention the TV monitor 54 is rotated by 90°. Accordingly, images produced from data commensurate with echos from the greatest depth within the breast or other object being examined will be at the bottom of the display and images of features closest to the surface will be at the top of the display.

While a preferred embodiment has been shown and described, various modifications and substitutions may be made thereto without departing from the spirit and scope of the invention. Accordingly, it is to be understood that the present invention has been described by way of illustration and not limitation.

What is claimed:

1. In apparatus for examining soft body tissue by means of the transillumination thereof with light comprising at least two selected wavelengths, the absorbtion of light at each of the selected wavelengths being measured, signals commensurate with the measured absorption being digitized and the resulting digital data being loaded into memory means at a first rate, said apparatus further including means responsive to the data commensurate with absorption which has been loaded into the memory means for generating a visually observable display commensurate with the said stored data, the improvement comprising:

ultrasound transducer means for transmitting ultrasonic energy into the tissue and receiving echos from within the tissue;

means connected to said transducer means for serially providing information in digital form commensurate with the reflection of ultrasonic energy from within the tissue, said digital information being generated at a second rate which is slower than said first rate;

means for serially receiving and storing a limited quantity of digitized signals from said information providing means;

a frame buffer, said frame buffer being connected to said means for serially receiving and storing, said frame buffer having a storage capacity commensurate with a full frame, said frame buffer being coupled to the memory means;

first address generator means for controlling the location in said frame buffer where the digitized signals are stored;

means for addressing said frame buffer means at the said first rate whereby information stored therein will be transferred into the memory means and stored in the same locations as occupied by data commensurate with the absorption of light at one of the selected wavelengths;

means responsive to information loaded into the memory means from said receiving and storing means for generating a television display commensurate with the stored information, said television display being an ultrasound image of the tissue being examined, said television display generating means including:

a television monitor;

video processor means, said processor means converting digital information received from the memory means to an analog analog input signal for said monitor; and means for selectively coupling said video processor means and the means for generating a visually observable display commensurate with the absorption of light to the memory means.

2. The apparatus of claim 1 further comprising:

means for generating data commensurate with alphanumeric information to be displayed simultaneously with the ultrasound image on said monitor; and means for storing said alphanumeric data in said memory means at the same locations as occupied by data commensurate with the absorption of light at the other selected wavelength.

3. The apparatus of claim 2 wherein said means for serially receiving and storing digitized signals comprises a FIFO.

4. Medical diagnostic apparatus comprising:

means for transilluminating body tissue with light comprising at least two selected wavelengths;

television camera means for sensing the transilluminated light, said camera means providing analog output signals commensurate with the absorption of light at said selected wavelengths;

means connected to said camera means for digitizing the analog signals generated thereby;

memory means coupled to said digitizing means for storing said digital signals, said memory means being synchronized with said transilluminating means whereby signals commensurate with the light at the two selected wavelengths will be stored at separately addressable memory locations, said signals commensurate with absorption being acquired and stored in said memory means at a first rate;

first display means, said first display means generating a visually observable display commensurate with the absorption of light at the selected wavelengths, said first display means being responsive to said stored signals commensurate with absorption;

ultrasound transducer means for coupling ultrasonic energy into the tissue and receiving echos from within the tissue, said transducer means generating signals corresponding to echos from within the tissue, said transducer means including a controllable ultrasound beam generator and means for sweeping the beam of ultrasound energy along a line, said transducer means generating signals said echo related at a second rate which is slower than said first rate;

means for digitizing the signals generated by said transducer means to produce digital information commensurate with received echos;

means for serially receiving and storing a limited quantity of said digital echo information, said receiving and storing means being coupled to said memory means;

means for addressing said means for serially receiving and storing at the said first rate whereby information stored therein may be loaded into said memory means;

second display means, said second display means generating a visually observable display constituting an ultrasound image of the tissue, said second display means being responsive to the stored digital echo related information; and means for selectively coupling said first and second display means to said memory means.

5. The apparatus of claim 4 wherein said first display means includes a color television monitor and said second display means includes a monochrome television monitor.

6. The apparatus of claim 5 wherein said means for serially receiving and storing digital echo information comprises:

means connected to said digitizing means for receiving and storing a limited quantity of information provided by said transducer means;

a frame buffer, said frame buffer being connected to said means for receiving and storing a limited quantity of information, said frame buffer having a storage capacity commensurate with a full frame; and first address generator means for controlling the location in said frame buffer where said digitized signals are stored.

7. The apparatus of claim 6 wherein said means for receiving and storing a limited quantity of information comprises a FIFO.

* * * * *